United States Patent [19]

Piran et al.

[11] Patent Number: 5,312,730
[45] Date of Patent: May 17, 1994

[54] IMMUNE COMPLEX TRANSFER WITH LYPOPHILIC BRIDGE

[75] Inventors: Uri Piran, Sharon; William J. Riordan, Boston; Deborah R. Silbert-Shostek, Stoughton, all of Mass.

[73] Assignee: Ciba Corning Diagnostics Corp., Medfield, Mass.

[21] Appl. No.: 889,321

[22] Filed: May 27, 1992

[51] Int. Cl.$^5$ ............... G01N 33/92; G01N 33/541; G01N 33/544
[52] U.S. Cl. ......................... 435/7.92; 435/961; 435/968; 435/971; 436/528; 436/540; 436/71; 436/829
[58] Field of Search ............ 435/7.92, 188, 961, 435/962, 965, 969, 971; 436/518, 540, 526, 71, 824, 829, 528

[56] References Cited

U.S. PATENT DOCUMENTS

| | | | |
|---|---|---|---|
| 4,434,236 | 2/1984 | Freytag | 436/512 |
| 4,828,981 | 5/1989 | Maggio | 435/7.22 |
| 4,971,904 | 11/1990 | Luddy | 435/7.1 |
| 5,009,998 | 4/1991 | Chow | 435/7.92 |

FOREIGN PATENT DOCUMENTS 0265244  4/1988 European Pat. Off. .
0303229  2/1989 European Pat. Off. .
0328829  8/1989 European Pat. Off. .
0399464 11/1990 European Pat. Off. .

OTHER PUBLICATIONS

E. Ishikawa et al, Development and applications of ultrasensitive enzyme immunoassays for antigens and antibodies, 185 Clinica Chimica Acta (1989) 223.
T. Kohno et al, Measurement of Anti–Thyroglobulin IgG in Serum by Novel and Sensitive Immune Complex Transfer Enzyme Immunoassay, 22 Clin Biochem (1989) 277.

Primary Examiner—Esther L. Kepplinger
Assistant Examiner—Nancy J. Parsons
Attorney, Agent, or Firm—Arthur S. Morgenstern; Nicholas I. Slepchuk, Jr.; Judith A. Roesler

[57] ABSTRACT

This invention relates to methods that have been found useful in reducing non-specific binding in immunochemical assays, via methods that can be implemented much faster than those used by Ishikawa. The techniques include the use of a lipophilic bridge, such as a liposome, or the elution of the antigen-antibody complex from the solid phase by the use of an anti-idiotypic antibody or an antibody, or the use of a heterologous reversible bridge.

10 Claims, 5 Drawing Sheets

IMMUNE COMPLEX TRANSFER WITH LYPOPHILIC BRIDGE

BACKGROUND

Over the past 30 years, immunochemical assays have become increasingly widespread. The most sensitive type of immunoassay is the solid phase (heterogeneous) immunoassay. However, it is desirable to increase sensitivity even further in order to be able to detect analytes which are present in lower levels than is presently possible to detect and to be able to detect more accurately the concentrations of the analytes. Sensitivity of the solid phase immunoassay is limited by several factors, including non-specific binding (NSB) of the tracer to the solid phase. The NSB is a result of either direct adsorption of the tracer to the solid phase surface, or indirect adsorption, via binding to non-specific components of the assay mixture that are adsorbed to the surface of the solid phase. These non-specific components are at least partially different than the material to be assayed, but have affinity toward the tracer. The adsorption of the non-specific components can lead to decreased sensitivity and also to reduced accuracy. One way of reducing NSB is to use a process called immune complex transfer (ICT), which was pioneered by Ishikawa. (See Ishikawa et al, 185 Clinica Chimica Acta (1989) 223; and Kohno et al, 22 Clin Biochem (1989) 277.)

In a conventional heterogeneous immunoassay, the assayed material (analyte) is incubated with a labeled specific binder (tracer) and an unlabeled, solid phase-immobilized specific binder. The incubation is followed by washing the solid phase to remove unreacted tracer, and measuring the signal associated with the ternary complex: solid phase-immobilized specific binder-/analyte/labeled specific binder. This measurement is done in the presence of the solid phase, and therefore includes the NSB. On the other hand, in the ICT assay, the ternary complex is eluted off of the solid phase and is measured in the absence of the solid phase and its associated NSB. Since some of the NSB is eluted as well, it is preferable to include in the ICT process a step in which the labeled complex is selectively recaptured with a new solid phase. This results in increased signal to noise ratio and higher assay sensitivity.

The ICT process requires elution of the immune complex under mild conditions, i.e. without breaking the bond formed between the analyte and the specific labeled binder. Also, the elution medium and elution conditions should not interfere with the recapture step. Ishikawa et al overcame this difficulty by constructing an immunochemical, reversible bridge between the solid phase specific binder and the solid phase, rather than employing the usual permanent attachment. They permanently immobilized to the solid phase an antibody against dinitrophenyl residues (anti-DNP), separately attached to the specific binder dinitrophenyl residues and then combined the two reagents to form a solid phase-immobilized specific binder. This provided a reversible immunochemical bond that could be broken by addition of excess dinitrophenyl-lysine (DNP-lys)

Although the use of solid phase immobilized anti-DNP/dinitrophenylated specific binder as the solid phase reagent by Ishikawa et al successfully reduced NSB, the method has two drawbacks: the major difficulty is the lengthy incubation with DNP-lys required for the elution step. Reducing the incubation time of this step is highly desirable in order to both obtain a quicker assay result and to minimized loss of sensitivity due to the time-dependent dissociation of the bond between the analyte and the labeled specific binder. A second difficulty is the added complexity, expense and instability associated with constructing the immunochemical bridge.

SUMMARY

This invention relates to methods that have been found useful in reducing non-specific binding in immunochemical assays, via methods that can be implemented much faster than those used by Ishikawa. The techniques include the use of a lipophilic bridge, such as a liposome, or the elution of the antigen-antibody complex from the solid phase by the use of an anti-idiotypic antibody or an antibody, or the use of a heterologous reversible bridge.

DETAILS OF THE INVENTION

Immune complex transfer (ICT) is a technique first used by Ishikawa for reducing non-specific binding (NSB) in immunoassays. The fluctuations of the NSB constitute background noise, which, if eliminated or reduced, would increase signal to noise ratio and, therefore, increase sensitivity, allowing the detection of much lower concentration of analyte. Since the method of elution of the immune complex used by Ishikawa et al is slow (1–4 hours) and cumbersome, the three novel ICT systems which have been developed in the present invention represent a significant improvement.

Throughout this discussion of ICT (including the examples), although there are mostly references to cases in which the analyte is an antigen, it should be noted that the description also applies to cases where the analyte is an antibody. When the analyte is an antigen, both of the specific binders are antibodies, and when the analyte is an antibody, both of the specific binders may be antigens (or an antigen mimic, such an antiidiotype or a genetically engineered antigen) or one specific binder is an antigen and the other is an antibody. This is due to the fact that the primary intention here is to discuss ICT reaction schemes, and there is little difference in whether the analyte is an antigen or an antibody. We shall use the term "specific binder" to refer to both antigen and antibody, and it should be noted that "binding partner" is also used in the literature as a synonym for "specific binder".

Several terms used throughout this patent will be defined in order to make their meaning clear. (1) Heterologous means an antigen which is used to react with an antibody, wherein the antigen is not the same antigen as that used to create the antibody. Thus, even though the heterologous antigen has some chemical similarity to the original antigen, it has lower affinity to the antibody. In addition, heterologous can also apply to other reaction pairs aside from antigens and antibodies. For example, a heterologous reaction pair similar to the homologous pair avidin-biotin is the reaction pair iminobiotin-avidin. (2) Antiidiotypic antibody is an antibody formed to a second antibody, at or very near to the binding site of the second antibody. (3) Immune complex is the entity which is dissociated from one solid phase and reconnected to a second solid phase in the purification scheme which is the subject of this invention. As can be seen from the discussion herein, the immune complex in some cases consists of the analyte to which at least one specific binder containing a label is attached. In other cases, the immune complex additionally consists of a second specific binder attached to the analyte. The species moving from one solid phase to the other is referred to as the separated complex. Furthermore, all of the examples discussed herein demonstrate the reattachment to the second solid phase via the analyte. However, the reattachment to the second solid phase could also occur via another component of the immune complex. (e.g., unlabeled specific binder, if present, or the label itself).

Other variations of the composition of the immune complex and the method in which it becomes attached to the solid phases will be apparent to those skilled in the art. (4) Accuracy means the reduction of systematic error caused by interferences. (5) Sensitivity refers to the ability to detect low levels of an analyte.

Furthermore, due to the presence of several options, it is possible to use several ICT cycles, each using a different chemistry or different method, to reduce the NSB even further. For example, one could use a lipophilic bridge during the first cycle, releasing and then recapturing on a heterologous solid phase, releasing and recapturing again, etc.

The solid phase reagent comprises an antibody (or, in some cases, an antigen) immobilized on insoluble particles (also referred to as the solid phase), such as paramagnetic particles, in order to aid in the separation of the antigen-antibody complex that is formed. Other insoluble matrices, such as glass beads, plastic reaction wells, etc. are also presumed to be acceptable. The reaction scheme also involves the use of a label, such as a radioactive label, chemiluminescent label, enzyme label, etc. The type of label used is not critical to our discussion. Many label systems are known in the art at present, and many new ones will undoubtedly be discovered in the future. Unless otherwise specifically stated, all label systems are presumed to be acceptable.

The discussion also refers to techniques well-known in the art, such as the reaction of small molecules to larger ones in order to generate a molecule which is large enough to elicit antibodies. Details of these techniques are not presented here and are presumed to be familiar to those knowledgeable in the art.

This technique is useful not just for immunochemical assays but also for many other binding assays, for example, for receptor assays and lectin assays. (In these cases, specific binder would refer to receptor or to lectin and other definitional and related changes would be necessary.) However, this technique cannot be used for gene probe assays unless the harsh conditions under which they are conducted are eliminated.

Additional alternatives can be used with the novel procedures. For example, if there is difficulty in using MNP-anti DNP as the complexing pair in the heterologous immunochemical bridge method, it is possible to use other binding pairs, such as iminobiotin-avidin.

Another alternative includes the presence of optional components between the analyte and the solid phase. In some cases, portions of this optional component are removed along with the analyte when it is being eluted from the first solid phase and reattached to the second solid phase. Other alternatives will become apparent to those with knowledge in this area.

One of the new techniques, the use of antiidiotypes, eliminates a further disadvantage encountered in using the Ishikawa method, i.e., the requirement of using secondary antibodies. In the antiidiotype procedure, the primary antibody is immobilized on the solid phase, thus requiring less labor to prepare, and it has been found to be more stable.

The benefits found in the novel system were unexpected. In a conventional immunoassay, the immobilized (unlabeled) antibody needs to be firmly attached to the solid phase or else it will dissociate while running the assay or during storage of the product. The problems encountered during the running of the assay have been most noticeable in the past during the wash steps, while the problems encountered during storage of the products have limited their commercial viability. The firm attachment found in Ishikawa's DNP system appears to be responsible for the slow release that was found. The novel systems provide fast release and, at the same time, an attachment that is firm enough to allow for a functional assay.

Three novel ICT systems have been developed. These systems are improvements over past techniques in that they are faster (less than 1 minute up to 30 minutes) and in some cases less complex (easier to produce reagents). Each system will be illustrated by a reaction system utilizing the novel principle. However, the examples used to illustrate the systems should not be considered to limit the usefulness or breadth of the ICT systems.

In the heterologous bridge system, an anti-hapten, such as an anti-DNP, is permanently immobilized on the solid phase. To the specific binder, instead of attaching the homologous hapten (DNP), a heterologous hapten, such as mononitrophenyl residue (MNP) or trinitrophenyl residue (TNP), is attached. This heterologous immunochemical bridge was surprisingly found to be stable enough to serve as an immunoassay reagent, but when excess DNP-lys is added, it is broken much faster than the homologous bridge. See the reaction scheme below and the detailed description of the assay in Example 1.

Reaction scheme for Method 1 involving a heterologous immunochemical bridge

Reagents for assay of CKMB:

1. First solid phase - Anti-CKMM is derivatized with MNP, which binds to anti-DNP on paramagnetic particles. The bond between anti-DNP and MNP is reversible.
2. Tracer - Anti-CKMB is derivatized with acridinium ester as a chemiluminescent label.
3. Second solid phase - Anti-CKBB immobilized on paramagnetic particles.

Figure 1:
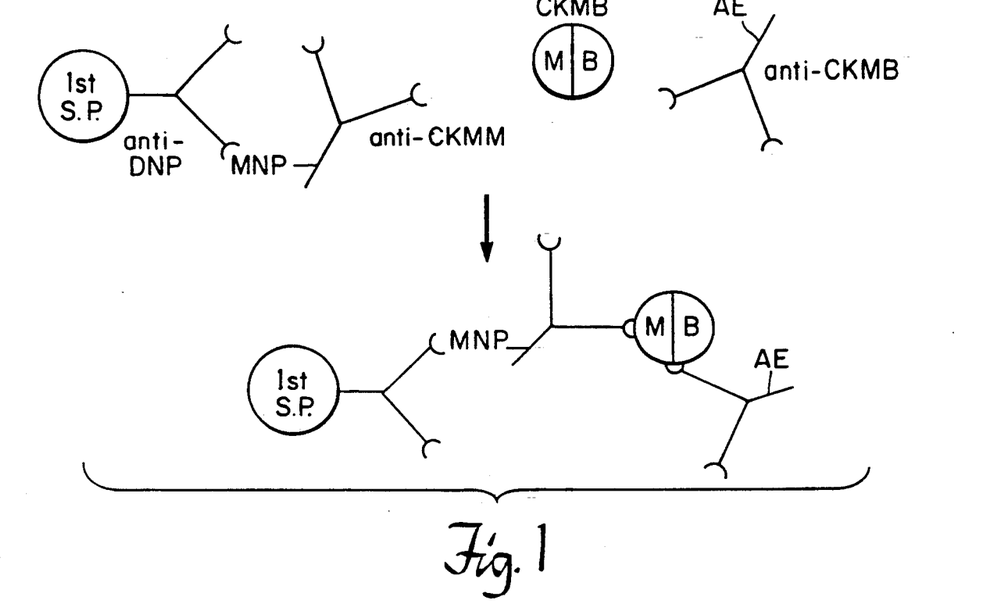
FIG. 1 in the heterologous bridge method, an immune complex is formed of anti-CKMM, which is attached to the first solid phase via MNP-anti-DNP, analyte CKMB and tracer.
Figure 2:
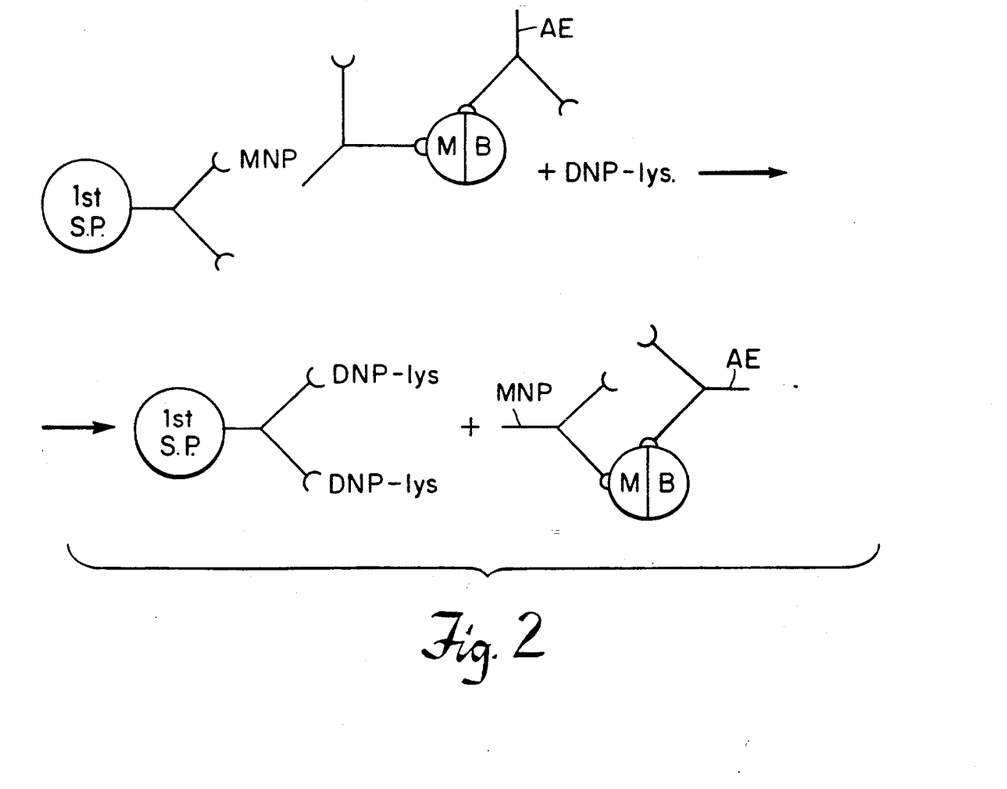
FIG. 2 in the heterologous bridge method, the immune complex is eluted from the first solid phase by incubation with DNP-lys.
Figure 3:
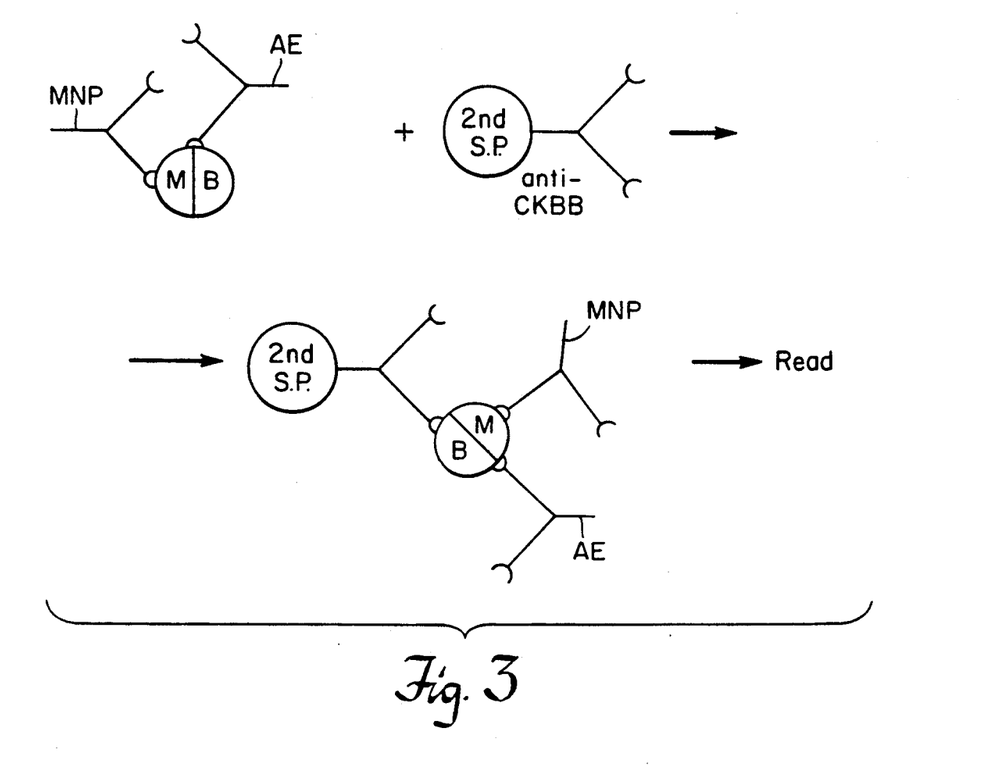
FIG. 3 in the heterologous bridge method, the immune complex is recaptured by anti-CKBB bound to a second solid phase.

Assay procedure:

a. First solid phase, analyte CKMB and tracer are incubated to form the immune complex on the solid phase.
See FIG. 1.
(Note that several abbreviations are used in the figures. S. P. refers to solid phase; M/B refers to CK MB, where CK is creatine kinase; DNP refers to dinitrophenol or dinitrophenyl; MNP refers to mononitrophenol; AE refers to acridinium ester.)

b. The immune complex is eluted from the first solid phase by incubation for 10 min with DNP-lys. The immune complex can be either separated from the first solid phase (e.g., transferred from the first test tube) or, alternatively, the second solid phase can be added to the first test tube, provided that the two solid phases can be later separated from each other, for example, if one particle has magnetic properties or differs in some other physical property from the first particle.
See FIG. 2.

c. The eluted immune complex is recaptured by the second solid phase and read in a luminometer.
See FIG. 3.

Aside from the illustration shown above for the heterologous scheme, it is possible to vary the system considerably, for example using markers aside from luminescent markers and other variations which are apparent to those with expertise in the art.

In the antiidiotype system, the solid phase-immobilized specific binder can be permanently immobilized on the solid phase as in a conventional assay, thus obviating the need for constructing a reversible bridge. Elution of the immune complex is done by addition of excess of an antibody against the analyte or an antiidiotypic antibody or a partial analyte mimic or a fragment derived from them. (A partial analyte mimic is a substance that contains a sufficient portion of the epitope of the analyte such that it can compete with the analyte for binding sites on the unlabeled antibody and, as such, cause the analyte to separate from the unlabeled antibody.) Previous attempts toward this end were done using adding a solution of an antibody identical to the one immobilized on the solid phase. These attempts showed that due to the strength of the interaction between the solid phase-immobilized antibody, displacement by a competing antibody is very slow, in the order of several hours or days. Applicants have found that, with some rare combinations of antibody/antigen pairs, it is possible to obtain considerable elution within 30 minutes incubation. Even more surprising was the applicants' finding that an antiidiotypic antibody of the immobilized antibody is faster and more efficient as an eluting agent. An additional surprising finding was that, if instead of adding an antibody that is identical to the immobilized one, a closely related antibody is added, elution is faster. In addition, this system is easy to manufacture, since there is no need to construct a reversible bridge between the antibody to the analyte and the solid phase. (See reaction scheme below and the detailed description in Example 2.)

Reaction scheme for Method 2 involving elution with an antiidiotype

Reagents for assay of CKMB:

1. First solid phase - Anti-CKBB immobilized on paramagnetic particles.
2. Tracer - Anti-CKMB labeled with acridinium ester.
3. Second solid phase - Anti-CKMM immobilized on paramagnetic particles.

Figure 4:
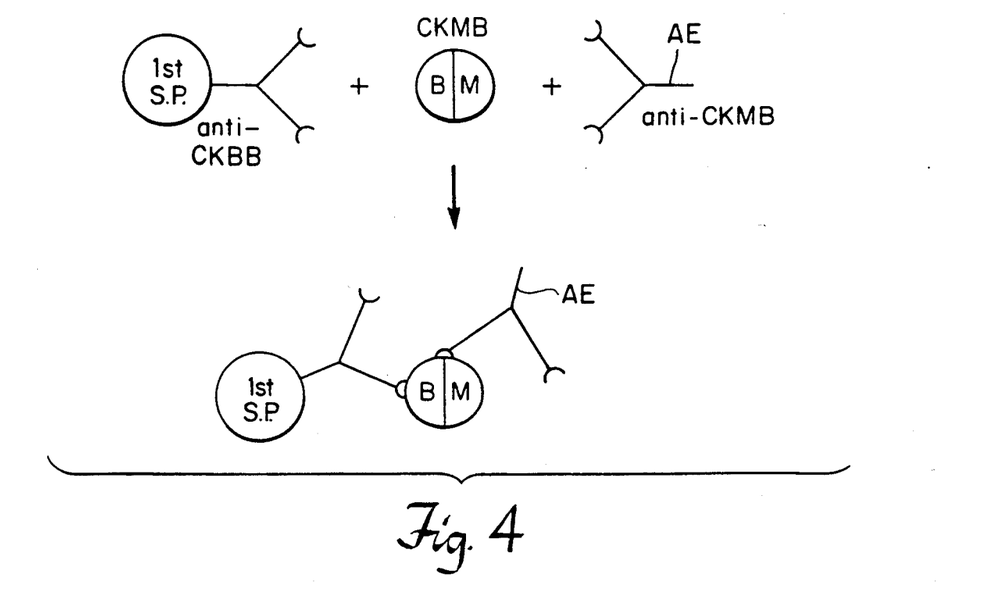
FIG. 4 in the anti-idiotype method, an immune complex is formed of anti-CKBB bound to the first solid phase, analyte CKMB and tracer.
Figure 5:
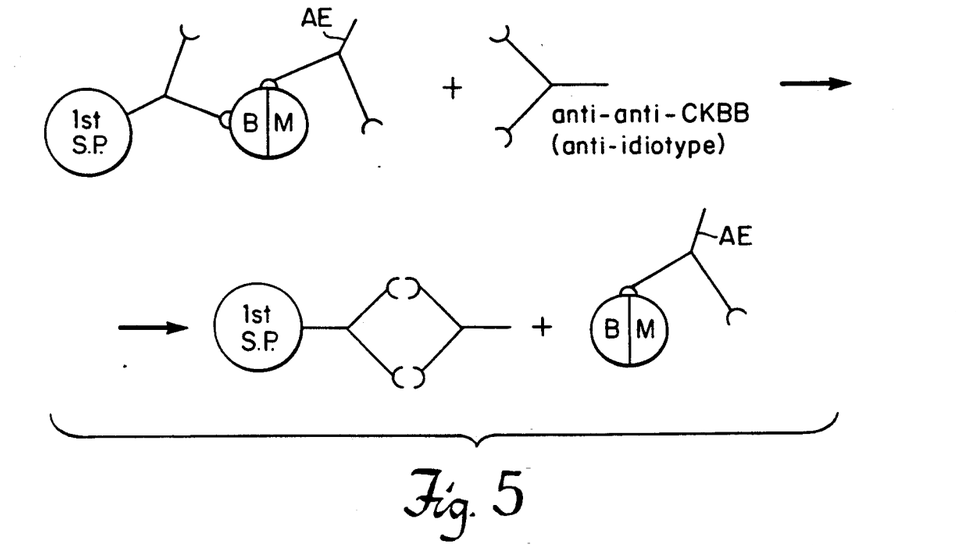
FIG. 5 in the anti-idiotype method, the immune complex is eluted from the first solid phase by incubation with anti-idiotypic antibody (anti-anti-CKBB).
Figure 6:
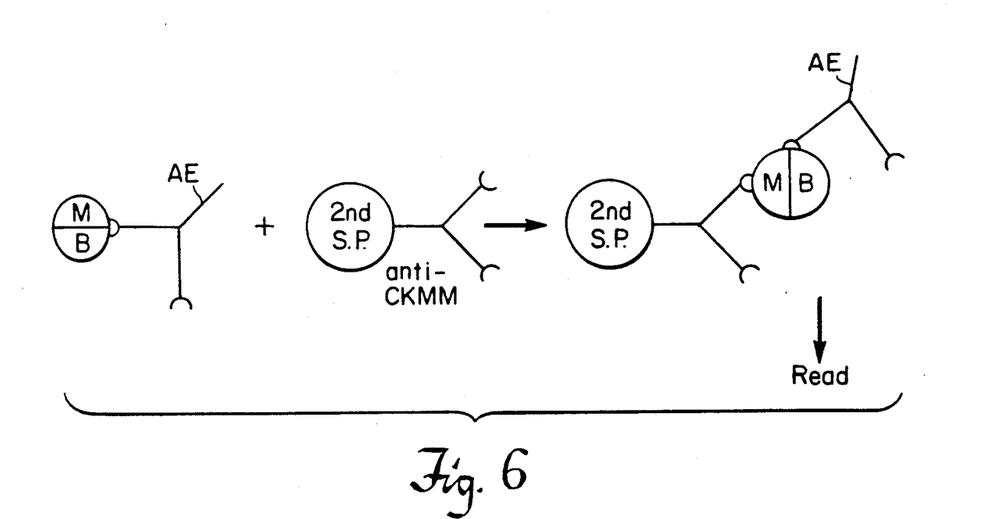
FIG. 6 in the anti-idiotype method, the immune complex is recaptured by anti-CKMM bound to the second solid phase.

Assay procedure:

a. First solid phase, analyte CKMB and tracer are incubated to form the immune complex on the first solid phase.
See FIG. 4.

b. The immune complex is eluted from the first solid phase by incubation for 30 min with antiidiotypic antibody (anti-anti-CKBB).
See FIG. 5.

c. The eluted immune complex is recaptured by the second solid phase and read in a luminometer.
See FIG. 6.

A third type of bridge system developed in the present invention involves a lipophilic bridge. Aggregates of lipophilic compounds, such as liposomes, lipoproteins, emulsions, hexagonal phases, micelles, bilayers and monolayers of certain compositions can be dispersed within seconds by detergents or certain enzymes. The use of a liposome or another lipophilic material as a bridge between the solid phase and the specific binder provides a stable attachment during the assay. Elution of the immune complex can then be rapidly obtained by addition of detergent. As an example, the reaction scheme of a system using liposomes is shown below, and detailed results using a liposome bridge is described in Example 3.

Reaction scheme for Method 3 involving a liposomal bridge Reagents for an assay of CKMB:

1. First solid phase - Anti-CKMM and DNP residues are covalently attached to liposomes. The liposomes are immunochemically bound to anti-DNP on paramagnetic particles.
2. Tracer - Anti-CKMB labeled with acridinium ester.
3. Second solid phase - Anti-CKBB immobilized on paramagnetic particles.

Figure 7:
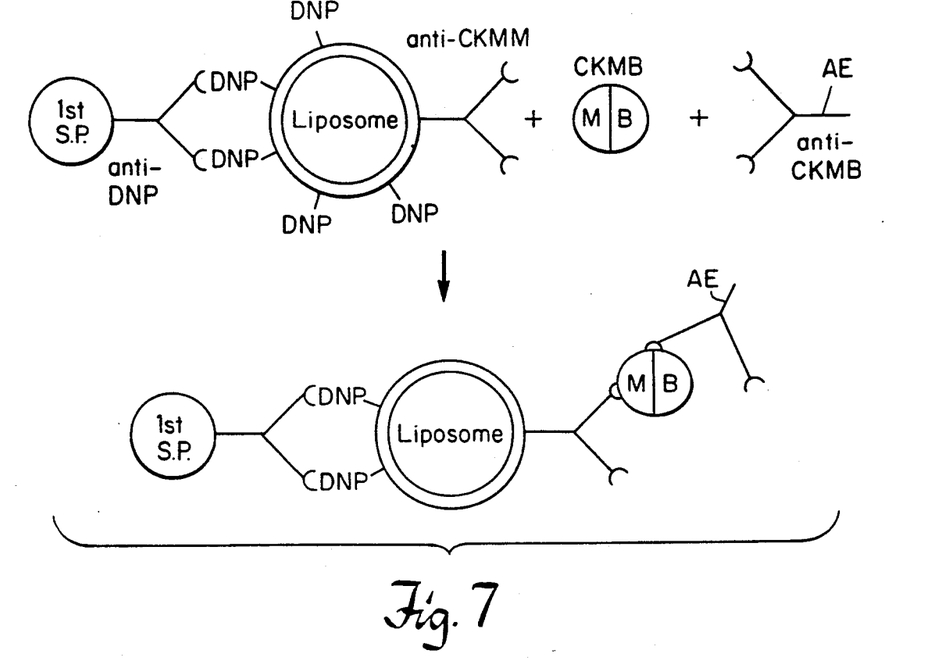
FIG. 7 in the liposomal bridge method, an immune complex is formed of first solid phase, liposomes with anti-CKMM on the surface, analyte CKMB and tracer.
Figure 8:
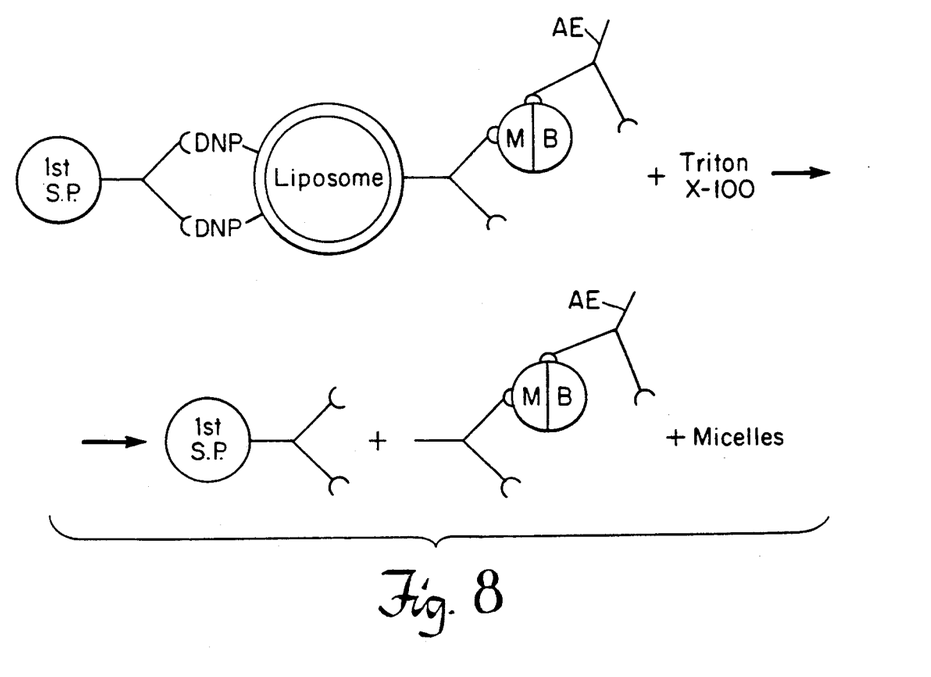
FIG. 8 in the liposomal bridge method, the immune complex is eluted from the first solid phase by incubation with detergent.
Figure 9:
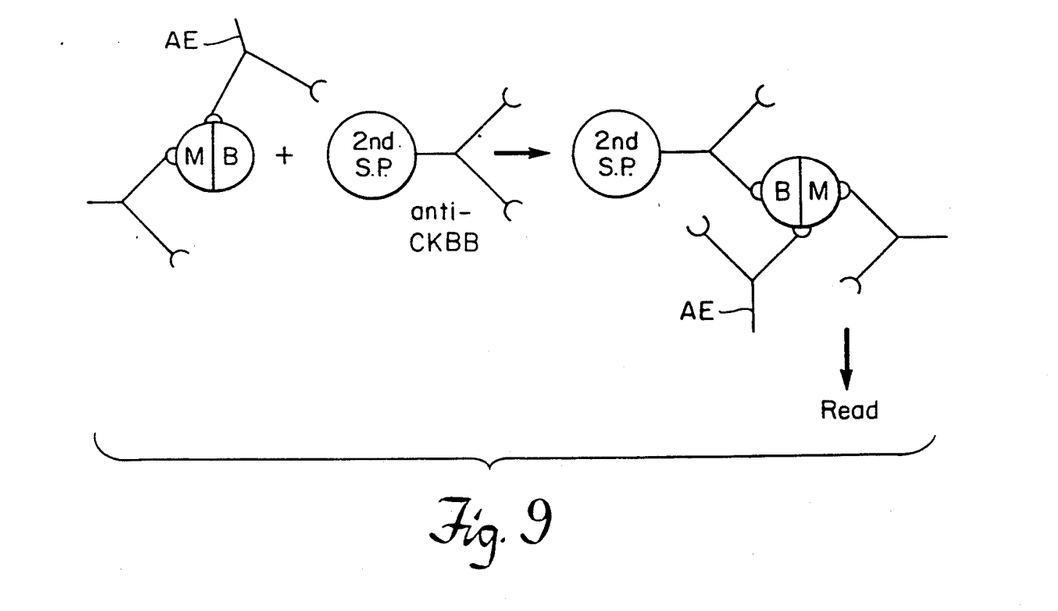
FIG. 9 in the liposomal bridge method, the immune complex is recaptured by anti-CKBB bound to a second solid phase.

Assay procedure:

a. First solid phase, analyte CKMB and tracer are incubated to form the immune complex on the solid phase.
See FIG. 7.

b. The immune complex is eluted from the first solid phase by incubation for 1 min with 0.1% Triton X-100 detergent. (The elution was actually completed within a few seconds, but, because the assay was conducted manually, it was not possible to terminate this step in any less than one minute.)
See FIG. 8.

c. The eluted immune complex is recaptured by the second solid phase and read in a luminometer.
See FIG. 9.

The following are provided to exemplify the application of the above development but are not intended to limit its usefulness.

EXAMPLE 1

Heterologous bridge a. Preparation of monoclonal antibodies.

Monoclonal antibodies were produced in mice (strain A/J) by immunizations and subsequent fusions of the splenocytes with Sp2/0-Ag 14 myeloma cells by the procedure described by Kohler and Milstein in Nature (London) Vol 256, pp. 494–497 (1975). Hybridoma cell secreting the desired antibodies were injected intraperitoneally into pristane-primed mice (strain CAF). Ascitic fluid from these mice was collected after 3–5 weeks. The antibodies were purified from the ascitic fluids by Protein A column chromatography using Affi-gel Protein A MAPS II Kit (Bio-Rad Laboratories, Richmond, Calif. 94801) according to the written protocol provided with the kit. The monoclonal antibodies against 2,4-dinitrophenol (DNP) were prepared by immunization with bovine serum albumin (BSA)-conjugated DNP. Preparation of monoclonals against creatine kinase isoenzymes MM, BB and MB was described by Piran et al. in Clinical Chemistry Vol. 33 pp. 1517–1520 (1987).

b. Immobilization of antibodies on paramagnetic particles.

Paramagnetic particles (PMP) were purchased from Advanced Magnetics, Inc. They were then activated by glutaraldehyde and conjugated to the various antibodies by the two-step glutaraldehyde procedure as described by Groman, E. V. et al. in BioTechniques, Vol. 3, pp. 156 (1985).

c. Conjugation of labels or haptens to proteins.

Antibodies were labeled with acridinium ester (AE) as follows: 250 μg antibody in 0.1 M sodium phosphate, 0.15 M sodium chloride, pH 8.0, was mixed with 50 μl of 2',6',-dimethyl-4'- (N-succinimidylcarbonyl)phenyl acridine-9-carboxylate (0.4 mg/ml) in dimethylformamide and incubated for 15 minutes at room temperature. 0.5 ml of a 10 mg/ml solution of DL-lysine was added to the mixture and the mixture was purified by gel filtration through a 10 ml column of Sephadex G-25. The labeled antibody appeared at the void volume of the column and was collected.

Other small molecules were conjugated to antibodies in a similar procedure. Dinitrophenol (DNP) was conjugated using N-hydroxysuccinimide- activated N-2,4-dinitrophenyl-b-alanine, mononitrophenol (MNP) was conjugated using N-hydroxysuccinamide- activated N-4-nitrophenol-b-alanine.

d. Release of Conjugated Antibodies from Solid Phase Particles.

DNP and MNP were conjugated to a monoclonal antibody against creatine kinase-MM (CKMM) using various ratios of small molecule to antibody The number of DNP and MNP molecules per antibody molecule was determined spectrophotometrically. Each conjugated antibody was radiolabeled with Iodine 125 using the Iodogen method.

Samples of each conjugate were incubated with a monoclonal antibody against DNP covalently coupled to PMP. After one hour incubation at room temperature, the PMP's were magnetically separated by a magnetic separation rack (Ciba Corning Diagnostics Corp., Medfield, Mass.), washed with 1 ml water and resuspended with a solution of 5 mM DNP-lysine. After 10 minutes incubation at room temperature with the DNP-lysine samples were magnetically separated and washed again, followed by counting in a gamma counter to determine the extent of displacement that had been achieved with the DNP-lysine solution.

The results are shown in the following tabulation:

| Small Molecule | # per Antibody | Percent Released in 10 min |
| --- | --- | --- |
| DNP | 6 | 10.6 |
| DNP | 12 | 3.2 |
| MNP | 8 | 73.1 |
| MNP | 14 | 65.3 |
| MNP | 24 | 85.1 | e. Immunoassay for CKMB with a heterologous bridge.

An anti-CKMM solid phase is formed by covalently coupling anti-DNP monoclonal antibody to PMP and then mixing this PMP with a MNP-derivatized mononclonal antibody against CKMM. After a one hour incubation period during which the conjugated anti-CKMM monoclonal antibody binds to the anti-DNP solid phase, the solid phase is magnetically separated and washed. A series of standards, controls and patient serum samples (0.1 ml each) are incubated for 30 minutes with this solid phase plus AE-labeled monoclonal anti-CKMB, in PBS/BSA buffer (50 mM sodium phosphate, 150 mM sodium chloride, 0.1% NaN3, 1 mM ethelenediaminetetraacetic acid, 1 mg/ml bovine serum albumin, pH 7.4). The reaction mixtures are then magnetically separated, washed to remove unbound AE-labeled antibody. The PMP-bound immune complexes are then mixed with 0.25 ml solution of 5 mM DNP-lysine, which initiates the release of the immune complexes from the solid phase by displacing the MNP conjugated antibody from the immobilized anti-DNP. After 10 minutes of the release step, the test tubes are placed on the magnetic separation rack for 3 minutes to magnetically separate the solid phase, and 0.2 ml of the supernatant, containing the released labeled immune complexes are aspirated and combined with a new solid phase consisting of PMP-immobilized anti-CKBB monoclonal antibody. Following capture of the AE-containing immune complex by the PMP-anti-CKBB the incubation mixture is magnetically separated, washed and the AE label is measured in a luminometer (Magic Lite Analyzer, Ciba Corning Diagnostics Corp. Medfield, Mass.).

EXAMPLE 2

Antibodies and antiidiotypes a. Preparation of monoclonal antibodies. Monoclonal antibodies against creatine kinase isoenzymes and thyroid stimulating hormone were prepared by immunizing mice with purified human creatine kinase isoenzymes and human TSH as described in Example 1, section a. The antibodies were labeled with AE or immobilized on PMP as described in Example 1, sections b and c.

Anti-idiotypic monoclonal antibody against anti-CKBB(CA8) was prepared as follows: Immunogen preparation: anti-CKBB monoclonal(CA8) was purified from ascites fluid by Protein A chromatography. The purified antibody was digested with pepsin to produce F(ab)'2 fragments. F(ab)'2 fragments were coupled to Keyhole Limpet Hemocyanin(KLH) using heterobifunctional cross-linker SPDP (Pierce Chemical Company, Rockford, Ill.).

Immunizations: A/J mice were immunized 3 times with 100 μg of F(ab)'2-KLH intraperitoneally. The first injection was in Complete Freund's Adjuvant. Subsequent immunizations were in Incomplete Freund's Adjuvant. Four days prior to the fusion, mice were immunized with 10 μg of antigen intravenously.

Cell fusion: Spleen cells from immunized mice were fused with SP2/O myeloma cells at a ratio of 5:1 according to protocol described by Kohler and Milstein in Nature (London) Vol. 256, pp. 494-497 (1975). Cell culture supernatants were screened for antibody production 7-21 days post fusion, when macroscopic colonies were observed. Positive cell lines, screened by method described below, were cloned by limiting cell dilution.

Screening procedure: F(ab) fragments were prepared by papain digestion of anti-CKBB(CA8), followed by purification on Protein A column. F(ab) fragments, at 10 μg/ml in PBS were adsorbed onto polystyrene tubes overnight at room temperature. Tubes were then washed and blocked with 1% BSA in PBS. Purified Protein A was labelled with AE.

Assay: Supernatants were incubated in F(ab) coated tubes for one hour at room temperature and then washed with water. AE-labeled Protein A was added to each tube. The incubation was continued for one hour at room temperature. Tubes were then washed and read in the luminometer. Supernatants giving a signal 10 times higher than background were considered positive and selected for further characterization.

Specificity testing: Anti-idiotypic monoclonals were tested for specificity in two ways. Coated tubes were made using two different monoclonals other than CA8, and anti-idiotypes were tested for binding in the Protein A assay described above. Anti-idiotypic monoclonals were positive on CA8 F(ab)s and negative on other F(ab)s.

Anti-idiotypic monoclonals were also shown to inhibit the binding of CA8 anti-CKBB Mab to AE-labeled CKBB.

b. Testing antibodies for ability to release immune complexes.

(1) CKMB assay

Various monoclonal antibodies against CKMM, CKBB, CKMB and TSH were tested to determine whether they could release the labelled complex AE-anti-MB-CKMB bound immunochemically to PMP-immobilized anti-CKBB. 100 μl serum standard containing either 0 or 45 ng/ml CKMB were incubated with 100 μl AE-anti-CKMB, input chemiluminescence 10 million relative light units (RLU's) and 500 μl PMP-immobilized anti-BB(CA8) for 1 hour.

The solid phases were magnetically separated and washed 2 times with deionized water. The PMP was then incubated with 0.25 ml PBS/BSA buffer (see Example 1 section e) containing 45 μg antibody for 30 minutes. The solid phases were separated and washed again and the remaining chemiluminescence was measured in the luminometer. The results are shown below:

| Antibody | RLU's Bound |
| --- | --- |
| buffer control (no antibody) | |
| zero CKMB | 2609 |
| 45 ng/ml CKMB | 212799 |
| Anti-BB(CA8) | |
| 0 | 2068 |
| 45 | 116045 |
| Antiidiotype anti-anti-CKBB(CA8) | |
| 0 | 2513 |
| 45 | 70182 |
| Anti-CKMM(13F10) | |
| 0 | 2232 |
| 45 | 229994 |
| Anti-CKBB(12A1) | |
| 0 | 2026 |
| 45 | 135814 |
| Anti-CKBB(5G12) | |
| 0 | 1947 |
| 45 | 198648 |
| Anti-CKBB(2D12) | |
| 0 | 1901 |
| 45 | 153813 |
| Anti-CKBB(8A2) | |
| 0 | 2125 |
| 45 | 148833 |
| Anti-CKMM(HH3) | |
| 0 | 1922 |
| 45 | 219011 |
| Anti-CKMM(GBB) | |
| 0 | 1919 |
| 45 | 226448 |
| Anti-CKMM(H44) | |
| 0 | 1862 |
| 45 | 216669 |
| Anti-TSH(2C10) | |
| 0 | 2043 |
| 45 | 225031 |
| Anti-CKMB(007) | |
| 0 | 2100 |
| 45 | 195705 |

Thus, specific and rapid release can be achieved by incubation with an antibody which is identical to the immobilized antibody (CA8) and to a lesser extent closely related anti-CKBB antibodies. Surprisingly, the antiidiotype (anti-CA8) was a more effective releasing agent than CA8 itself.

(2) TSH assay

Monoclonal antibodies against TSH, polyclonal anti-TSH, and monoclonals against CKMM and CKBB were tested to determine whether they could release AE labelled anti-TSH bound TSH complex from PMP-immobilized anti-TSH(2C10).

100 μl serum standard containing 0 or 6 μIU/L TSH were incubated with 100 μl AE-labeled anti-TSH(E21), 3.5 million RLU's total input label, for 2 hours. 500 μl of PMP-immobilized anti-TSH(2C10) was then added and incubated 30 min to form sandwich complex. The solid phase was magnetically separated and washed 2 times with deionized water.

Bound complex was then released by the incubation with 0.25 ml PBS/BSA containing 50 μg antibody for 30 minutes. The solid phases were separated, and washed 1 time with distilled water and the amount of AE-anti-TSH(2C10)-TSH complex remaining bound to the PMP was then measured in the luminometer.

| Releasing Antibody | RLU's Bound |
| --- | --- |
| Buffer control (no antibody) | |

-continued

| Releasing Antibody | RLU's Bound |
|---|---|
| 0 TSH | 1000 |
| 6 μIU/L TSH | 130581 |
| Anti-TSH(2C10) | |
| 0 | 1000 |
| 6 | 110702 |
| Polyclonal Anti-TSH | |
| 0 | 1000 |
| 6 | 117594 |
| Anti-TSH(E21) | |
| 0 | 1000 |
| 6 | 129175 |
| Anti-TSH(7A10) | |
| 0 | 1000 |
| 6 | 61624 |
| Anti-TSH(11A8) | |
| 0 | 1000 |
| 6 | 128003 |
| Anti-CKBB(CA8) | |
| 0 | 1000 |
| 6 | 132233 |
| Antiidiotype anti-anti-CKBB(CA8) | |
| 0 | 1000 |
| 6 | 131026 |
| Anti-CKMM(13F10) | |
| 0 | 1000 |
| 6 | 129680 |

Thus, addition of excess solution-phase capture antibody did not release appreciable amount of complex within the incubation time, but surprisingly, another anti-TSH(7A10) did.

c. CKMB immune complex transfer assay employing antiidiotype anti-anti-CKBB(CA8) or anti-CKBB as releasing agents.

100 μl CKMB standards were incubated with 100 μl AE-anti-MB(007) as a tracer (total counts 100 million RLU's) and 500 μl PMP-anti-BB(CA8) for 1 hour at room temperature. The solid phases were separated and washed 2 times with 1 ml deionized water. Anti-CKBB(CA8) or antiidiotype anti-CKBB(CA8), 10 μg in 0.25 ml PBS/BSA was added to the PMP's to release the labeled complexes from solid phase. The PMP were mixed and then incubated for 30 minutes at room temperature. They were then placed on the magnetic rack to magnetically separate the solid phase, and 0.2 ml of each supernatant was mixed with 500 μl of PMP-anti-CKMM(AH6). After 15 minutes incubation at room temperature the PMP's were separated, washed 1 time with deionized water and read in a luminometer.

The following tabulation shows the signal obtained for each CKMB serum standard in the assays involving release by anti-CKBB and the antiidiotypic antibody.

| Release by anti-CKBB | | Release by antiidiotype |
|---|---|---|
| RLU | CKMB ng/ml | RLU |
| 690 | 0.00 | 640 |
| 2595 | 0.45 | 2403 |
| 10025 | 4.50 | 10196 |
| 181318 | 45.00 | 155180 |

EXAMPLE 3

Liposome Bridge a. Preparation of the capture antibody anti-CKMM(13F10) immobilized on PMP via a liposomal bridge.

(1) Preparation of liposomes bearing dinitrophenyl groups.

Liposomes were prepared from a mixture of 85.5 μmol dioleoyl phosphatidyl choline, 7.35 μmol dioleoyl phosphatidyl glycerol, 1.0 μmol- dinitrophenylamineocaproic-dioleoyl phophatidylethanolamine (all from Avanti Polar Lipids, Inc., Birmingham, Ala.) and 4.0 μmol N-[4-(p-maleimidophenyl) butyryl]-phophatidlethanolamine (prepared as described by Martin, J. F. and Papahadjopoulos, D. 257 J. Biol. Chem. (1982) 286).

The lipids were dissolved in 3 ml chloroform in a small, clean petri dish. Chloroform was evaporated and the dry lipid mixture film was further lyophilized overnight in a desiccator under vacuum. The lipids were then hydrated with 10 ml of 2.7% v/v glycerol, 1 mM EDTA at pH 6.1 at room temperature to form large oligolamellar liposomes. These were extruded through polycarbonate membranes with pore diameters of 0.8, 0.6, 0.4 and 0.2 μm (Nucleopore) to form uniform vesicles. 10 ml PBS was added, and the liposomes were sedimented by ultracentrifugation and resuspended in 6 ml PBS to a final concentration of 16.67 μmol phospholipid per ml.

(2) Preparation of liposome-coupled anti-CKMM. Monoclonal anti-CKMM(13F10) was purified and dialyzed overnight against a buffer consisting of 50 mM acetic acid, 50 mM sodium phosphate, 5 mM EDTA and 50 mM sodium chloride at pH 6.1. Two ml of antibody solution (2.5 mg) was made 20 mM with respect to dithiothreitol and incubated 30 minutes at room temperature. The reduced antibody was then separated from excess dithiothreitol by gel filtration with 10 ml Sephadex G-25 column in PBS.

Liposomes were coupled to this antibody by mixing 5 mg antibody with 25 μmol phosphatidyl cholin. After 16 hour incubation at room temperature the liposome solution was washed 3× in 4 mls of PBS by ultracentrifugation. Finally the liposomes were resuspended in 2.5 mls of PBS.

(3) Binding of dinitrophenylated, antibody-bearing liposomes to PMP-immobilized anti-DNP. The liposomes prepared as described in section (3) were bound to PMP-immobilized anti-DNP by incubating 10 mg PMP with 10 μmol phosphatidyl cholin for 16 hours in 2 ml PBS at room temperature. The liposome-PMP mixture was then washed in equal volumes of PBS with 0.1% BSA to remove unbound liposomes and then resuspended to 100 μg PMP per ml of PBS/BSA for use in assay.

b. CKMB immune complex transfer assay.

CKMB serum standards, 0.1 ml each, were mixed with 0.1 ml of AE-labeled monoclonal anti-CKMB(007) consisting of 100 million RLU's in PBS/BSA. Anti-CKMM(13F10)-liposomes-PMP complex, prepared in section a (4) were then added in 0.5 ml PBS/BSA (50 μg PMP) and the mixtures were incubated for 1 hour at room temperature. The PMP's were then magnetically separated and washed with 1 ml of PBS/BSA three times, using a magic separation rack (Ciba Corning Diagnostics Corp.). The liposome bridge was then dissolved by addition of 0.25 ml of a 0.1% solution of Triton X-100 in deionized water, followed by immediate placement of the test tubes in the magnetic separation rack. A 0.2 ml aliquot of the supernatant solution, containing the released labeled immune complex was immediately transferred to fresh test tubes. To these tubes, 0.5 ml of PMP-immobilized anti-CKBB(CA8)

containing 50 μg PMP was immediately added and the tubes were incubated for 1 hour at room temperature in order to re-capture the immune complex. This PMP was magnetically separated and washed with 1 ml of PBS+BSA, followed by chemiluminescence readout in the luminometer. In a control experiment the PMP's were read in the luminometer before the addition of Triton X-100. Typical calibration curves are shown below:

| Control assay (no release/recapture) | | Assay with release/recapture | |
|---|---|---|---|
| CKMB ng/ml | RLU's | CKMB ng/ml | RLU's |
| 0 | 78626 | 0 | 958 |
| 0.45 | 117391 | 0.45 | 5721 |
| 4.50 | 258079 | 4.50 | 74069 |
| 45.00 | 1819078 | 45.00 | 721085 |

Thus the release of the immune complex using the liposomal bridge and a detergent, followed by recapturing the complex with a fresh solid phase led to reduction of background signal and increase in the signal/background ratio.

What is claimed is:

1. A rapid method for sensitive and accurate binding assay comprising
   a. reacting the analyte with
      1. a labeled specific binder for the analyte and
      2. a specific binder for the analyte which has been reversibly attached to a first solid phase via the use of a lipophilic material to form a labeled specific binder-analyte-specific binder-lipophilic material-first solid phase complex, wherein said lipophilic material provides a stable bridge between the solid phase and specific binder, and is readily dispersed by detergents or enzymes,
   b. separating the labeled specific binder-analyte-specific binder complex from the first solid phase with said detergents or enzymes,
   c. reattaching the labeled specific binder-analyte-specific binder complex to a second specific binder, which binds to the analyte or another component of the immune complex and which is attached to a second solid phase, and
   d. determining the amount of the analyte present by measurement of the amount of the labeled specific binder attached to the second solid phase.

2. A method of claim 1 wherein the binding assay is an immunochemical assay, a lectin assay or a receptor assay.

3. A method of claim 1 wherein the separation procedure (step b) is completed in 1 minute or less.

4. A method of claim 1 wherein the lipophilic material is a liposome, emulsion, hexagonal phase, micelle, bilayer, monolayer, or a combination of two or more of these materials.

5. A method of claim 4 where the reversible binding is achieved via the use of a liposome; the separation is achieved via the addition of a detergent; and the reattaching is achieved by attaching to the second solid phase an antibody to a material sufficiently similar to the analyte to form a second solid phase-antibody complex, such that the analyte is suitably captured by the second solid phase-antibody complex.

6. A method of claim 1 wherein the labeled specific binder is reacted with the analyte during the same step or a different step than the analyte is reacted with the specific binder-first solid phase complex.

7. A method of claim 1 wherein the separated complex is separated form the first solid phase during the same step or a different step than the separated complex is reattached to the second solid phase.

8. A method of claim 1 wherein the label consists of a radioactive label, a chemiluminescent label or an enzyme label.

9. A method of claim 8 wherein the label is an acridinium ester.

10. A method of claim 1 in which the binding assay is an immunochemical assay.

* * * * *